(12) United States Patent
Chen

(10) Patent No.: US 11,266,444 B2
(45) Date of Patent: Mar. 8, 2022

(54) EXTERNAL FIXATION DEVICE WITH ABSORPTION MATERIAL FOR REDUCING RADIOFREQUENCY INDUCED HEAT TRANSFER AND METHOD THEREOF

(71) Applicant: University of Houston System, Houston, TX (US)

(72) Inventor: Ji Chen, Sugar Land, TX (US)

(73) Assignee: UNIVERSITY OF HOUSTON SYSTEM, Houston, TX (US)

(*) Notice: Subject to any disclaimer, the term of this patent is extended or adjusted under 35 U.S.C. 154(b) by 118 days.

(21) Appl. No.: 16/248,738

(22) Filed: Jan. 15, 2019

(65) Prior Publication Data

US 2019/0150984 A1      May 23, 2019

Related U.S. Application Data

(63) Continuation-in-part of application No. 14/879,383, filed on Oct. 9, 2015, now Pat. No. 10,219,834, which is a continuation of application No. PCT/US2015/053319, filed on Sep. 19, 2015.

(60) Provisional application No. 62/113,271, filed on Feb. 6, 2015.

(51) Int. Cl.
| | |
|---|---|
| A61B 17/62 | (2006.01) |
| A61B 17/64 | (2006.01) |
| A61B 17/00 | (2006.01) |
| A61B 5/055 | (2006.01) |
| A61B 5/00 | (2006.01) |

(52) U.S. Cl.
CPC .............. *A61B 17/62* (2013.01); *A61B 5/055* (2013.01); *A61B 5/4851* (2013.01); *A61B 17/64* (2013.01); *A61B 5/4504* (2013.01); *A61B 2017/00831* (2013.01); *A61B 2017/00911* (2013.01)

(58) Field of Classification Search
None
See application file for complete search history.

(56) References Cited

U.S. PATENT DOCUMENTS

| | | | |
|---|---|---|---|
| 6,080,153 | A | 6/2000 | Mata et al. |
| 8,623,029 | B2 | 1/2014 | Bailey et al. |
| 9,050,605 | B2 | 6/2015 | Guo |
| 9,833,289 | B2 | 12/2017 | Schuele et al. |
| 2005/0085810 | A1 | 4/2005 | Lutz et al. |
| 2007/0270801 | A1 | 11/2007 | Am et al. |

(Continued)

OTHER PUBLICATIONS

Huang, X et al. MRI Heating Reduction for External Fixation Devices Using Absorption Material, article, 2014, pp. 113-117, IEEE.

(Continued)

*Primary Examiner* — Tessa M Matthews
(74) *Attorney, Agent, or Firm* — Winstead PC

(57) ABSTRACT

The present invention provides an external fixation device and method thereof. The device includes at least an insert for inserting into a patient's tissue such as a bone. The insert is fastened to a fastening assembly which comprises at least a RF heat source member during MRI scanning of the patient. At least a part of the RF heat source member's surface is covered with an absorption material to reduce the direct or indirect transfer of RF induced heat from the member to the insert. The absorption material has an electric conductivity greater than $10^{-4}$ S/m.

16 Claims, 20 Drawing Sheets

(56) References Cited

U.S. PATENT DOCUMENTS

| | | |
|---|---|---|
| 2008/0085810 A1 | 4/2008 | Hart et al. |
| 2009/0299368 A1 | 12/2009 | Bauer |
| 2010/0036466 A1 | 2/2010 | Min et al. |
| 2010/0174347 A1* | 7/2010 | Kieval ............... A61N 1/36117 |
| | | 607/116 |
| 2010/0174348 A1* | 7/2010 | Bulkes .................... A61N 1/05 |
| | | 607/116 |
| 2010/0298827 A1 | 11/2010 | Cremer et al. |
| 2012/0089142 A1 | 4/2012 | Mullaney |
| 2012/0226277 A1 | 9/2012 | Tan et al. |
| 2014/0058389 A1* | 2/2014 | Singh .................... A61B 17/66 |
| | | 606/56 |
| 2014/0210472 A1 | 7/2014 | Homann et al. |
| 2014/0275959 A1* | 9/2014 | Disegi ................... A61B 5/055 |
| | | 600/410 |
| 2016/0038185 A1* | 2/2016 | Disegi ................... A61B 17/60 |
| | | 606/59 |

OTHER PUBLICATIONS

Liu, Y et al. Effect of Insulating Layer Material on RF-Induced Heating for External Fixation System in 1.5 T MRI System, article, Jun. 11, 2013, pp. 223-227, 33(3), Electromagnetic Biology and Medicine.

Liu, Y et al. Numerical Investigations of MRI RF Field Induced Heating for External Fixation Devices, article, Feb. 9, 2013, pp. 1-14, 12(12), BioMedical Engineering OnLine.

\* cited by examiner

EXTERNAL FIXATION DEVICE WITH ABSORPTION MATERIAL FOR REDUCING RADIOFREQUENCY INDUCED HEAT TRANSFER AND METHOD THEREOF

CROSS-REFERENCE TO RELATED APPLICATIONS

This application is a Continuation-in-Part of U.S. application Ser. No. 14/879,383 filed on Oct. 9, 2015 and issued as U.S. Pat. No. 10,219,834, which claims priority to U.S. Application No. 62/113,271, filed on Feb. 6, 2015, and International Application No. PCT/US2015/053319, filed on Sep. 19, 2015, the contents of all of which are incorporated herein by reference in their entireties.

FIELD OF THE INVENTION

The present invention generally relates to an external fixation device with absorption material for reducing radiofrequency induced heat transfer and method thereof. Although the invention will be illustrated, explained rand exemplified with a distraction osteogenesis ring system and a model fixation device, it should be appreciated that the present invention can also be applied to other fields, for example, computer assisted circular ring fixation system for the treatment of limb deformity correction, hybrid fixator-proximal tibia frame using rings with clamps, modular knee bridge, Delta frame ankle bridge, and pelvic frame, among others.

BACKGROUND OF THE INVENTION

External fixation is a surgical treatment used to stabilize bone and soft tissues at a distance from the operative or injury focus. The device gains its popularity because it causes minimal damage to soft tissues. On the other hand, there is an increasing trend to use magnetic resonance imaging (MRI) because of its non-ionized feature and high-resolution image quality. However, strong radio frequency (RF) fields generated by MRI systems can cause heating effects when patients are being scanned. This can be a significant issue when patients with metallic medical devices (e.g., external fixation devices) are scanned. Localized energy can be deposited near the tips of these medical devices, which may potentially lead to permanent tissue damage. This is particularly severe when patients with an external fixation device are being scanned for the fact that most external fixation devices are made up of nonmagnetic metal to maintain mechanical strength. When a typical external fixation device undergoes MRI, the metallic parts will interact strongly with the electromagnetic field and may produce induced electromagnetic energy inside human subjects. Furthermore, because only a small portion of metallic components are inside the human body, whereas the major portion of the device is outside, the highly condensed electromagnetic energy can only dissipated in a limited volume of tissue, which results in a very high increase in local temperature inside the human body. Luechinger et al. evaluated a group of large external fixation clamps and frames in MR environment and found a maximum of 9.9° C. increase in the local temperature at the tip of metallic pin inside the patient's tissue. See, e.g., J. Biomed. Mater. Res. B, Appl. Biomater., 2007, 82:17-22.

To reduce the high-risk temperature increase, the method of using electrical (not thermal) absorption material to change the heating distribution was considered. Liu et al. studied the effect of electrical insulated layer material, and found it as a potential way to reduce the induced RF heating. See, e.g., Lie et al., Electromagnetic Biology and Medicine, 2014, Vol 33, No. 3, Pages 223-227. However, the capability of insulated layer for RF heat reduction is limited, as the operating radio frequencies are relatively high (commonly above 64 MHz) and the induced current can still couple inside the human body.

Therefore, there exists a need to overcome the aforementioned problems. Advantageously, the present invention provides a solution that effectively reduces the RF heating (or RF-induced heating) in external fixation devices.

SUMMARY OF THE INVENTION

One aspect of the present invention provides an external fixation device comprising:
(1) at least an insert for inserting into a patient's tissue such as a bone, and
(2) a fastening assembly, to/with which the insert is fastened/secured/connected. The fastening assembly comprises at least a RF heat source member, and at least a part of the member's surface is covered with an absorption material to reduce or diminish transferring or dissipating of RF induced heat from the source member to the insert directly, or indirectly, i.e. via other component(s) in the fastening assembly. Generally, the absorption material has an electric conductivity greater than $10^{-4}$ S/ms. During MRI scanning, a RF heating at the insert, particularly at the portion of the insert that is within the patients tissue/bone, such as a tip of an insert pin, is significantly reduced as compared to the RF heating in the absence of the absorption material.

In some embodiments, the external fixation device of the invention does not include, or excludes, an external fixation device comprising at least two bars, at least two clamps, at least two pins, and an absorption material between at least a bar and at least one clamp, or between at least one clamp and at least one pin, wherein the absorption material has an electric conductivity in the range of $10^{-2}$-100 S/m, and wherein a RF heating at a tip of the pins is significantly reduced compared to that in an external fixation device without an absorption material between at least a bar and at least one clamp, or between at least one clamp and at least one pin, as claimed, described, and illustrated in co-pending U.S. application Ser. No. 14/879,383 filed on Oct. 9, 2015, the content of which is incorporated herein by reference in its entirety.

Another aspect of the invention provides a method for reducing RF-induced heating in an external fixation device comprising:
(1) providing an external fixation device comprising (i) at least an insert for inserting into a patient's tissue such as a bone and (ii) a fastening assembly, wherein the fastening assembly comprises at least a RF heat source member;
(2) covering at least a part of the member's surface with an absorption material to reduce transferring or dissipating of RF induced heat from the member to the insert, directly or indirectly, i,e via other component(s) in the fastening assembly, wherein the absorption material has an electric conductivity greater than $10^{-4}$ S/m; and
(3) fastening the insert to the fastening assembly.

The above features and advantages and other features and advantages of the present invention are readily apparent from the following detailed description of the best modes for carrying out the invention when taken in connection with the accompanying drawings.

BRIEF DESCRIPTION OF THE SEVERAL VIEWS OF THE DRAWINGS

The patent or application file contains at least one drawing executed in color Copies of this patent or patent application publication with color drawing(s) will be provided by the Office upon request and payment of the necessary fee.

The present invention is illustrated by way of example, and not by way of limitation, in the figures of the accompanying drawings and in which like reference numerals refer to similar elements. All the figures are schematic and generally only show parts which are necessary in order to elucidate the invention. For simplicity and clarity of illustration, elements shown in the figures and discussed below have not necessarily been drawn to scale. Well-known structures and devices are shown in simplified form, omitted, or merely suggested, in order to avoid unnecessarily obscuring the present invention.

DETAILED DESCRIPTION OF THE PREFERRED EMBODIMENT

In the following description, for the purposes of explanation, numerous specific details are set forth in order to provide a thorough understanding of the present invention. It is apparent, however, to one skilled in the art that the present invention may be practiced without these specific details or with an equivalent arrangement.

Where a numerical range is disclosed herein, unless otherwise specified, such range is continuous, inclusive of both the minimum and maximum values of the range as well as every value between such minimum and maximum values. Still further, where a range refers to integers, only the integers from the minimum value to and including the maximum value of such range are included. In addition, where multiple ranges are provided to describe a feature or characteristic, such ranges can be combined.

It is also to be understood that the terminology used herein is for the purpose of describing particular embodiments only, and is not intended to limit the scope of the invention. For example, when an element is referred to as being "on", "connected to", or "coupled to" another element, it can be directly on, connected or coupled to the other element or intervening elements may be present. In contrast, when an element is referred to as being "directly on", "directly connected to", or "directly coupled to" another element, there are no intervening elements present.

Figure 1A:
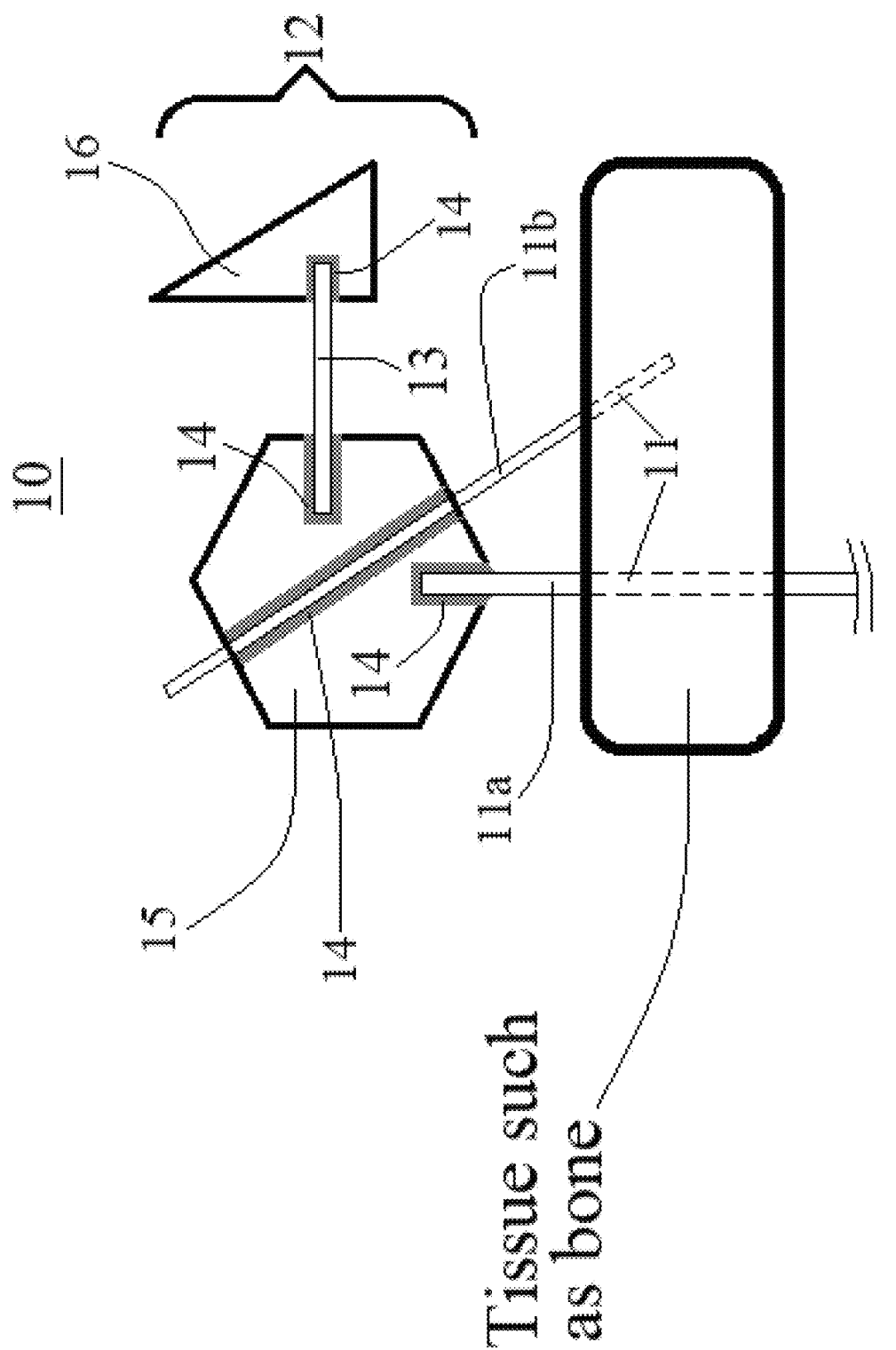
FIG. 1A schematically illustrates an external fixation device in accordance with an exemplary embodiment of the present invention.

As shown in FIG. 1A, a fixation device 10 includes (1) a fastening assembly 12 and (2) at least an insert 11 for inserting into a tissue such as a bone. The insert 11 may be a pin, a through wire, or a screw such as a Schanz screw. The insert 11 can be an insert 11a that penetrates through the tissue, and/or an insert 11b that does not penetrate through the tissue. The fastening, assembly 12 may include one or more RF heat source members such as rods, bars, rings, clamps, threaded rods and nuts, wire bolts, connection bolts/joints, external fixation pins, standoffs, locking hinges, angular distractors, linear distractors, connecting plates, speed nuts, supports, and washers, and optionally one or more non-RF heat source members (e.g. a mere heat transfer channel). As shown in FIG. 1A, RF heat source members and non-RF heat source members may include one or more components with reference numbers 13, 15 and 16.

The insert 11 is removably fastened, secured or connected to the fastening assembly 12. The absorption material 14 may be in the form of a film, a layer, a cushion, a coating, and a seal tape. For example, the absorption material 14 may be an intermediate layer or an interfacial film (A) between a RF heat source member and another component (either a RF heat source member or not) within the fastening assembly 12 that would directly contact the RF heat source member in the absence of the layer or film 14; (B) between the insert 11 and a RF heat source member that would directly contact the insert 11 in the absence of the layer or film 14; and/or (C) between the insert 11 and a non-RF heat source member (e.g. a mere heat transfer channel) in the fastening assembly 12 that would directly contact the insert in the absence of the layer or film 14.

For example, the fastening assembly 12 may include a member or component 13 made of an electrically conductive material, which may become a source of RF induced heat during MRI scan. At least a part of the surface of the member 13 is covered (either loosely or adhesively e.g. by coating) with absorption material 14, like a cushion, to reduce or block the transfer of RF induced heat from the member 13 to the insert 11, directly or indirect (e.g. via an intermediate component 15). The fastening assembly 12 may include a subassembly 15 such as a combination clamp or a ring to fasten or secure both the member 13 and the insert 11 together. In such embodiments, the combination clamp or ring 15 may also become a RF heat source member like 13, or they may become a medium that transfers RF heat from other sources like 13 to the insert 11. Then, the absorption material 14 may be placed between subassembly 15 and member 13, and/or between subassembly 15 and insert 11. If member 13 is connected to other RF heat source component(s) 16 within the fastening assembly 12, then the absorption material 14 may be placed between component(s) 16 and member 13 as well.

The absorption material 14 may have an electric conductivity in the range of from X to Y, wherein X<Y; X is selected from $10^{-4}$ S/m, $10^{-3}$ S/m, $10^{-2}$ S/m, $10^{-1}$ S/m, $10^{0}$ S/m, $10^{1}$ S/m and $10^{2}$ S/m; and Y is selected from $10^{-3}$ S/m, $10^{-2}$ S/m, $10^{-1}$ S/m, $10^{0}$ S/m, $10^{1}$ S/m, $10^{2}$ S/m and $10^{3}$ S/m.

In various exemplary embodiments, when the absorption material 14 has an electric conductivity in the range of $10^{-4}$-$10^{3}$ S/m, its dielectric constant or is preferably in the range of about 4-9 such as 5-9. In contrast, when the absorption material 14 has an electric conductivity lower than $10^{0}$ S/m such as lower than $10^{-1}$ S/m, its dielectric constant εr is preferably in the range of about 1-4 such as 1-3 or 2-3. Generally, the absorption material 14 has a thickness of not greater than 10 mm.

The absorption material 14 is chemically different from all the components (either RF heat source members or non-RF heat source members) in the fastening assembly, such as rods, bars, rings, clamps, threaded rods and nuts, wire bolts, connection bolts/joints, external fixation pins, standoffs, locking hinges, angular distractors, linear distractors, connecting plates, speed nuts, supports, and washers. The absorption material 14 is commercially available from Molex Incorporated (Lisle, Ill., USA).

Figure 1B:
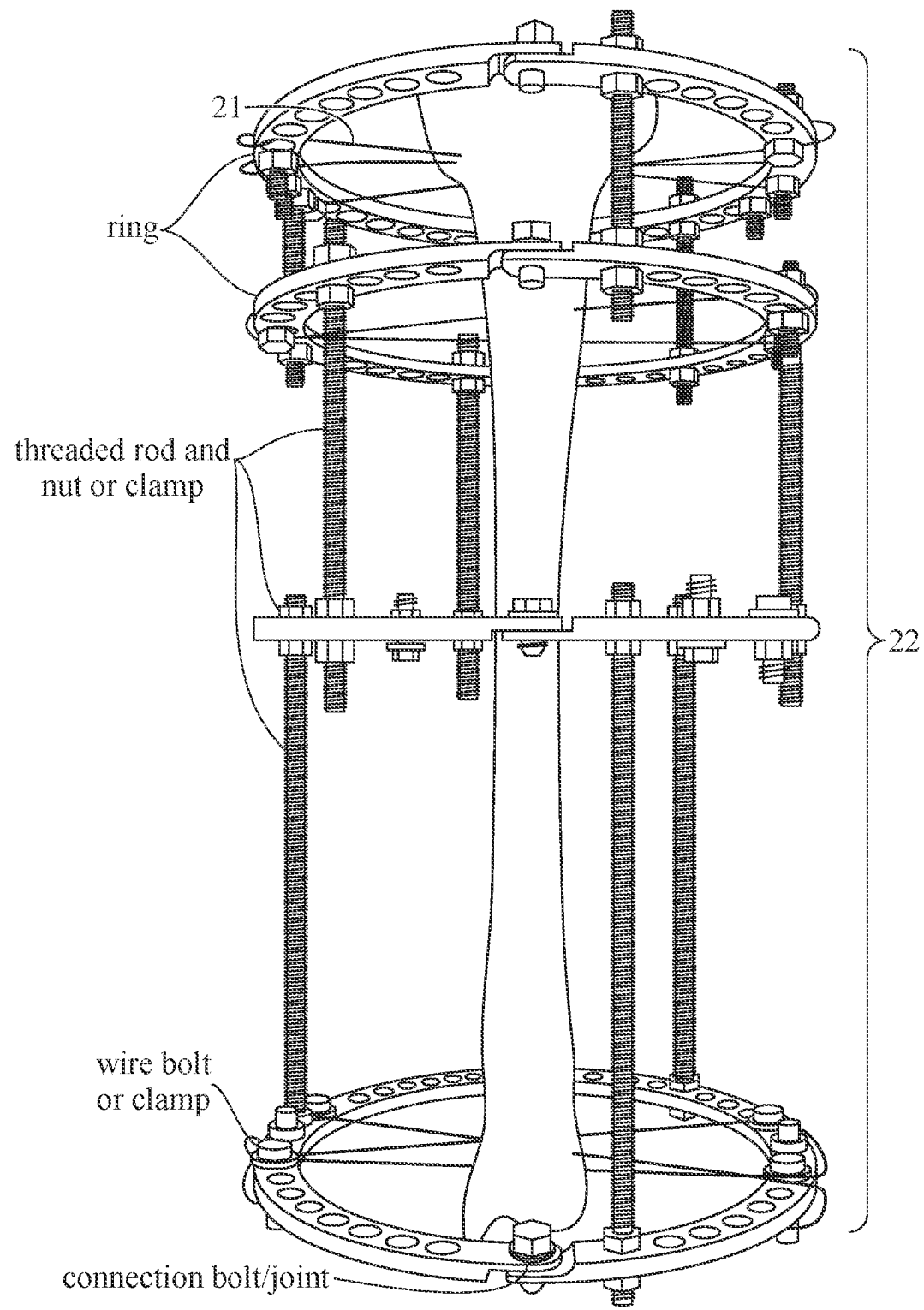
FIG. 1B shows a distraction osteogenesis ring system in accordance with an exemplary embodiment of the present invention.

FIG. 1B shows a representative ring fixation system named "Distraction Osteogenesis Ring System", commercially available from DePuy Synthes Ring fixators are used for fracture management and deformity correction, and are most commonly applied to the tibia, the femur, the humerus, the foot, the hand and the forearm. The system in Figure B includes transfixion wire (or pin, or Schanz screw) 21 made of metal such as stainless steel, which is an embodiment of insert 11 in FIG. 1A. Wires 21 are fastened to the fastening assembly 22 that includes various components such as rods, bars, rings, clamps, threaded rods and nuts, wire bolts, connection bolts/joints, external fixation pins, standoffs, locking hinges, angular distractors, linear distractors, connecting plates, speed nuts, supports, and washers. All or a part of these components may generate RF induced heat during MRI scanning, and are subject to the "covering" of absorption material 14 according to the present invention.

In various exemplary embodiments, the rings can be made of titanium alloy or carbon fiber, and in the form of half rings, full rings, ⅝ rings, femoral arches and foot rings. For example, two half rings may be placed around the limb, and then connected to each other with two connection bolts/joints. These rings are attached to each other with carbon fiber threaded rods and nuts to create a frame as shown in FIG. 1B, or with carbon fiber struts (not shown) to create a frame in computer assisted circular ring fixation system for the treatment of limb deformity correction, which is also commercially available from DePuy Synthes. An operator can use 3-4 threaded rods and nuts and 8 mm/11 mm wrench to connect the rings. Preferably, these rings remain parallel to each other after they are connected. If holes in the rings do not line up properly, such as when different diameter rings are used, then spherical washer couples, locking hinges or connecting plates may be used to connect the threaded rods to adjacent rings.

In various exemplary embodiments, the transfixion wires 21 may be smooth and reduction or "olive". In wire insertion (Schanz screw insertion), an alcohol-soaked sponge may be used to guide and cool the wire. Preferably, an operator does not start the drilling until the wire tip makes contact with the bone and stops drilling as soon as the tip protrudes from the far cortex of the bone. The wires are inserted perpendicular to the longitudinal axis of the affected limb, from the side with the most vulnerable anatomy. Then the frame is positioned or moved into the proper position along the wire. The frame sits with the rings perpendicular to the long axis of the bone. Schanz screws may be used in the place of wires, or with wires (usually one Schanz screw in the place of one wire on a ring. Appropriate Schanz screw (self-tapping, self-drilling, hydroxyapatite) or Steinmann pin should be selected for the patient's bony anatomy.

In various exemplary embodiments, external fixation pins are attached to rings that encircle the affected limb. In wire fixation, wire bolts such as offset wire bolts or slotted wire bolts are used to connect the wire to the ring. The wire is placed between the bolt head and the ring. If the wire does not contact the ring without bending, then spacing washers may be used between the bold head and ring, or wire posts may be used. The operator may then fasten the bolts with standard or square nuts. In other embodiments, such as hybrid fixator-proximal tibia frame commercially available from DePuy Synthes, wires 21 may be attached to the ring, using adjustable wire/pin clamps.

The absorption material 14, in the form of a film, a layer, a cushion, a coating or a seal tape and with a desirable thickness, may be introduced into the Distraction Osteogenesis Ring System as shown in FIG. 1B, at any suitable interfacial space between any two structural components in the assembly 22, or between wire 21 and a component the wire 21 directly contacts to, for reducing or eliminating the transfer or dissipation of RF heat from assembly 22 to wire 21. In other words, the absorption material 14 prevents or alleviates the wire from becoming a "RF heat sink" of assembly 22 during MRI scanning. For example, the absorption material 14 may be (1) a seal tape between the rings' holes and the threaded rods or struts designed to attach to the rings; (2) a film between wires 21 and their wire bolts such as offset wire bolts or slotted wire bolts that are used to connect the wires 21 to the ring; (3) a layer between the wire bolts and the ring holes; (4) a cushion between wire 21 and a bolt head and the ring; (5) a film between a clamp and wire 21; (6) a film between the clamp and the ring; and (7) a seal tape between or among any suitable components in assembly 22 such as between a bolt and a nut.

In the following, the present invention will be exemplified and illustrated with a model external fixation device that comprises at least two pins, and the fastening assembly comprises at least two bars and at least two clamps. The absorption material is placed between at least a bar and at least one clamp, or between at least one clamp and at least one pin. Therefore, these embodiments provide methods for reducing RF-induced heating in an external fixation device including at least two bars, at least two clamps and at least two pins, wherein the methods each include adding or using or introducing an absorption material between at least one bar and at least one clamp, or between at least one clamp and at least one pin. These embodiments further provide external fixation devices, each including at least two bars, at least two clamps, at least two pins, and an absorption material between at least a bar and at least one clamp, or between at least one clamp and at least one pin, wherein the RF heating at the pins' tips is significantly reduced compared to that in an external fixation device without an absorption material between at least a bar and at least one clamp, or between at least one clamp and at least one pin.

In some embodiments, the absorption material is in the form of a film and serves as intermediate between at least one bar and at least one clamp, or between at least one clamp and at least one pin. In some other embodiments, the absorption material is in the form of a film and completely or partially covers the area of at least a bar to which at least one clamp is connected, or the area of at least a pin to which at least one clamp is connected. In some other embodiments, the absorption material is in the form of a film and completely covers the area of at least a bar to which at least one clamp is connected, or the area of at least a pin to which at least one clamp is connected. For example, the absorption material covers the area of every connection point between a bar and a clamp, or between a clamp and a pin.

In still some other embodiments, the absorption material has an electric conductivity between that of a perfect electric conductor and an insulator. For example, the absorption material has an electric conductivity in the range of $10^{-4}$-$10^{3}$ S/m, in the range of $10^{-3}$-$1.0$ S/m, or in the range of $10^{-2}$-$10^{-1}$ S/m). In still some other embodiments, the absorption material has a permittivity $\varepsilon_r$ in the range of about 1 to $10^{10}$. In yet still some other embodiments, the absorption material has a thickness of not greater than 10 mm.

Using an absorption material with a specific conductivity and permittivity between the clamps and pins, or between the clamps and bars, of an external fixation device can result in substantial reduction of RF induced heating. The conductivity and permittivity of the absorption material can be optimized to maximize the reduction of RF induced heating.

A fast optimization process based on Response Surface Methodology (RSM) scheme can be applied in finding the desired conductivity and permittivity to achieve the optimum heating reduction. The RF induced heating can be quickly reduced by choosing correct factors along steepest descent direction in RSM process. Both permittivity and conductivity have impacts on heating-reduction effect.

Figure 1C:
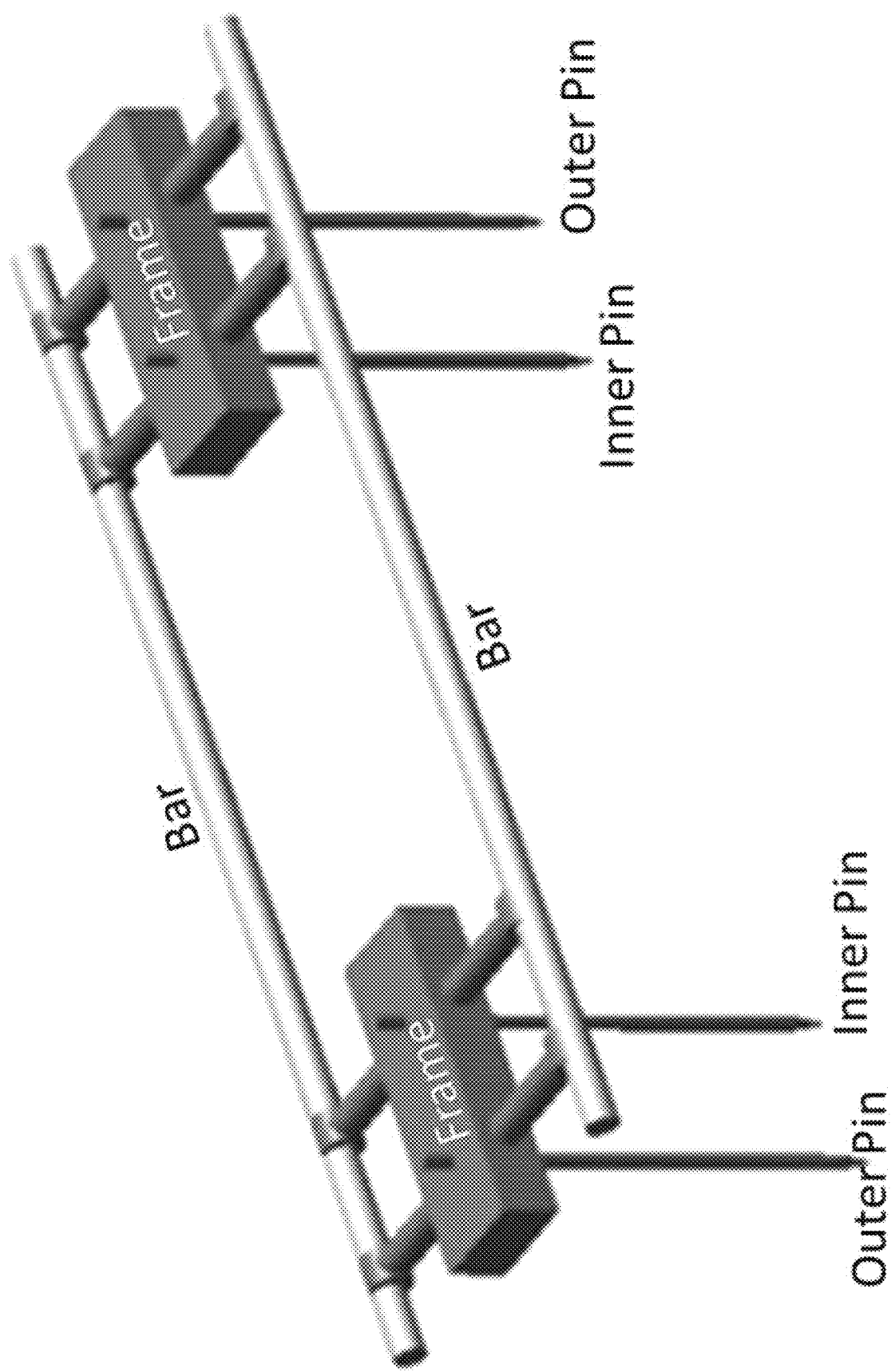
FIG. 1C shows the model of an external fixation device for testing in accordance with an exemplary embodiment of the present invention.

The external fixation device includes at least two connection bars, at least two stabilizing clamps between the two bars, at least one pin in each clamp that extends and penetrates into a human body to securely position the fixation device relative to the human body. As shown in FIG. 1C, the external fixation device includes two connection bars (parallel as shown), two clamps, and four pins (one inner pin and one outer pin in each of the two clamps), all of which are labeled and identified in FIG. 1C. In this example, the lower part of the pins, including their tips, are immersed in a human body to secure the device's relative position to the human body.

The present embodiments provide a novel and efficient solution to reduce RF induced heating in an external fixation device by utilization of an absorption material between different parts in the external fixation device. Not intended to be bound by the theory, it is believed that the conductive absorption material changes the electric field distribution around and on the external fixation devices, consumes itself a certain amount of power outside the human body, and thereby reducing the RF-induced heating.

It is desirable to find the optimum electrical absorption characteristics for heat reduction, however doing so requires testing all combinations of multiple factors for the best absorption material parameters, i.e., conductivity and permittivity, to minimize RF-induced heating. One approach for testing different absorption materials and calculating the heating reduction is One-Variable-At-a-Time (OVAT), i.e., single variable is varied at a time while other variables are kept fixed. This approach requires great resources to obtain a limited amount of information that can be used for the method of this invention. For multi-variable optimization, the OVAT method is inefficient and sometime even unreliable. To overcome this limitation, a statistical method called Response Surface Methodology (RSM) can also be used in Design of Experiment (DoE) techniques. DoE has been widely accepted and utilized in industry. A number of successful applications of DoE have been reported by many US and European manufacturers over the last 25 years or so. See, e.g., D. C. Montgomery et al., Engineering Statistics, 2nd edition, John Wiley & Sons, 2001, New York. As another method, RSM can also be used to identify the optimum set of conditions of the absorption materials that can be used in the methods and devices of this invention as well. Heating effect can be minimized by using the RSM optimization process quickly. With current technology, the absorption characteristics of the materials can be adjusted for the specific external fixation device by needs. This approach makes absorption material practical in engineering.

To practice the methods in the embodiment, simulations and experiments are used to evaluate the effect of an absorption material in reducing RF induced heating of external fixation devices. To accurately analyze this effect, systematic descriptions of both simulation and experiment setup will be specified. All procedures described below conform to requests from US Food and Drug Administration (FDA) to provide valid data, which are described by ASTM International in Standard Test Method For Measurement Of Radio Frequency Induced Heating Near Passive Implants During Magnetic Resonance Imaging, ASTM standard, F2182-11, West Conshohocken, Pa. (ASTM International: 2011).

A. Absorption Material

The absorption materials that can be used for this embodiment are glossy so that the reflected electromagnetic (EM) waves can be reduced, or eliminated. For single frequency RF heating evaluation, the absorption characteristics can be considered as electrical conductivity. For evaluation of their effectiveness in practicing this embodiment, absorption materials with a conductivity ranging from $10^{-4}$ to $10^3$ S/m were used.

B. Heating Effect Evaluation

Developed in 1948 by Peones, the "Peones Bioheat Equation" (PBE) with certitude is the most accepted formula for thermal BioEM simulations. The formula is:

$$\rho c \frac{\partial T}{\partial t} = \nabla \cdot (k \nabla T) + \rho Q + \rho SAR - \rho_b c_b \rho \omega (T - T_b)$$

where k is the thermal conductivity, SAR is the specific absorption rate, ω is the perfusion rate and Q is the metabolic heat generation rate. ρ is the density of the medium, ρb, cb and $T_b$ are the density, specific heat capacity and temperature of blood, respectively.

From this equation, induced RF heating effects are commonly related to Specific Absorption Rate (SAR). It is widely accepted to use SAR as index of power deposition which is proportional to heating. Hereinafter, the 1 g spatial-averaged SAR will be used to evaluate RF induced heating effects numerically. Unless defined otherwise, SAR is referred to the 1 g spatial-averaged SAR in W/kg.

C. Simulation Model: External Fixation Device, ASTM Phantom and MRI RF Coil

As mentioned above, an embodiment of the external fixation device includes clamps, pins and connection bars. Generic external fixator models were developed to study the RF heating effects in the MRI environment, as shown in FIG. 1C which is a top-side view of a fixation device of the embodiment. It includes three parts: 1) two metallic blocks to represent the clamps; 2) two connection bars between the clamps; and 3) four pins which are screwed into the bones of a patient during surgery, with one inner pin and one outer pin in each of the two clamps as shown in FIG. 1C. As an illustrative example, the metallic block has the dimension of 11.4 cm by 2 cm by 3.75 cm, the pin has a diameter of 0.5 cm and length of 16 cm, and the connection bar has a diameter of 1.1 cm and a length of 41.5 cm, and 2 cm insertion depth from the surface of the phantom is kept constant for all studies.

Figure 2:
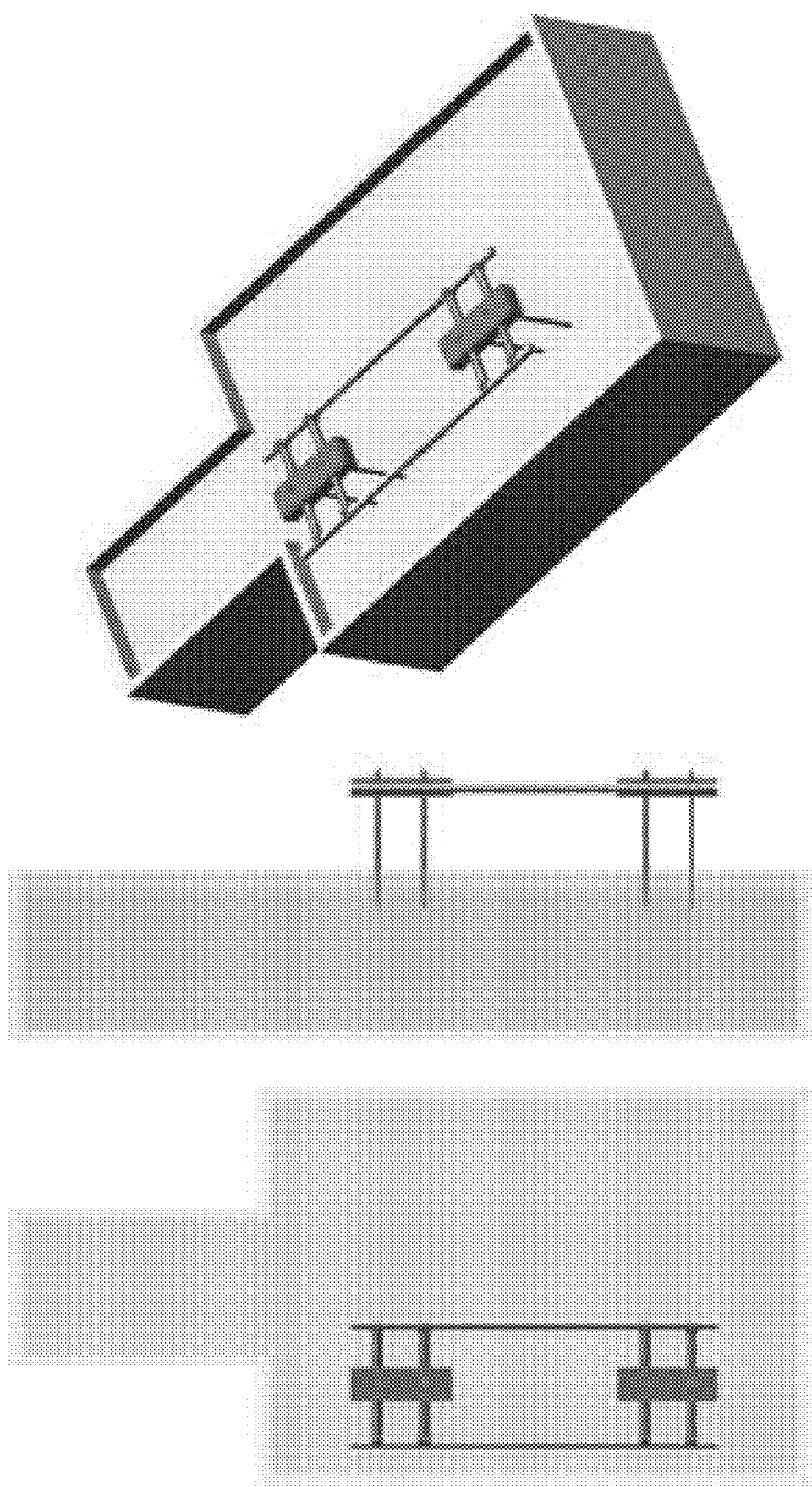
FIG. 2 shows the relative locations of an external fixation device and ASTM phantom in accordance with an exemplary embodiment of the present invention.
Figure 3:
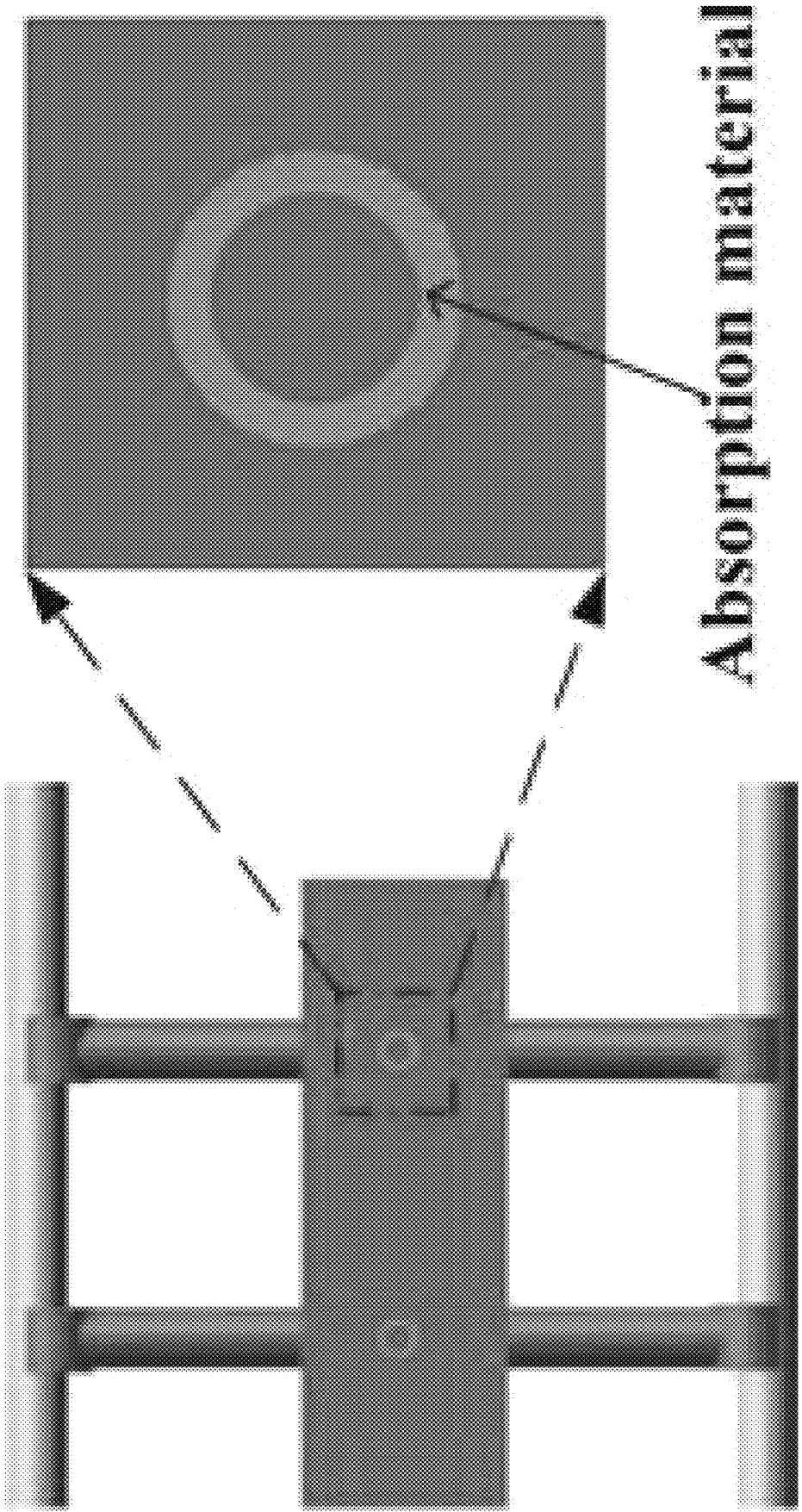
FIG. 3 illustrates absorption material geometry on external fixation devices in accordance with an exemplary embodiment of the present invention.

In this study, a device is placed at a location where high incident tangential electric field is observed. See FIG. 2 which provides top and side views of the relative locations of external fixation and ASTM phantom. The absorption material is modeled as a tubular structure with 5 mm inner diameter and 7 mm outer diameter placed between the block and pin. Detailed structure for the device model is shown in FIG. 3, which shows and labels absorption material geometry in the clamps of an external fixation device of this embodiment.

Figure 4:
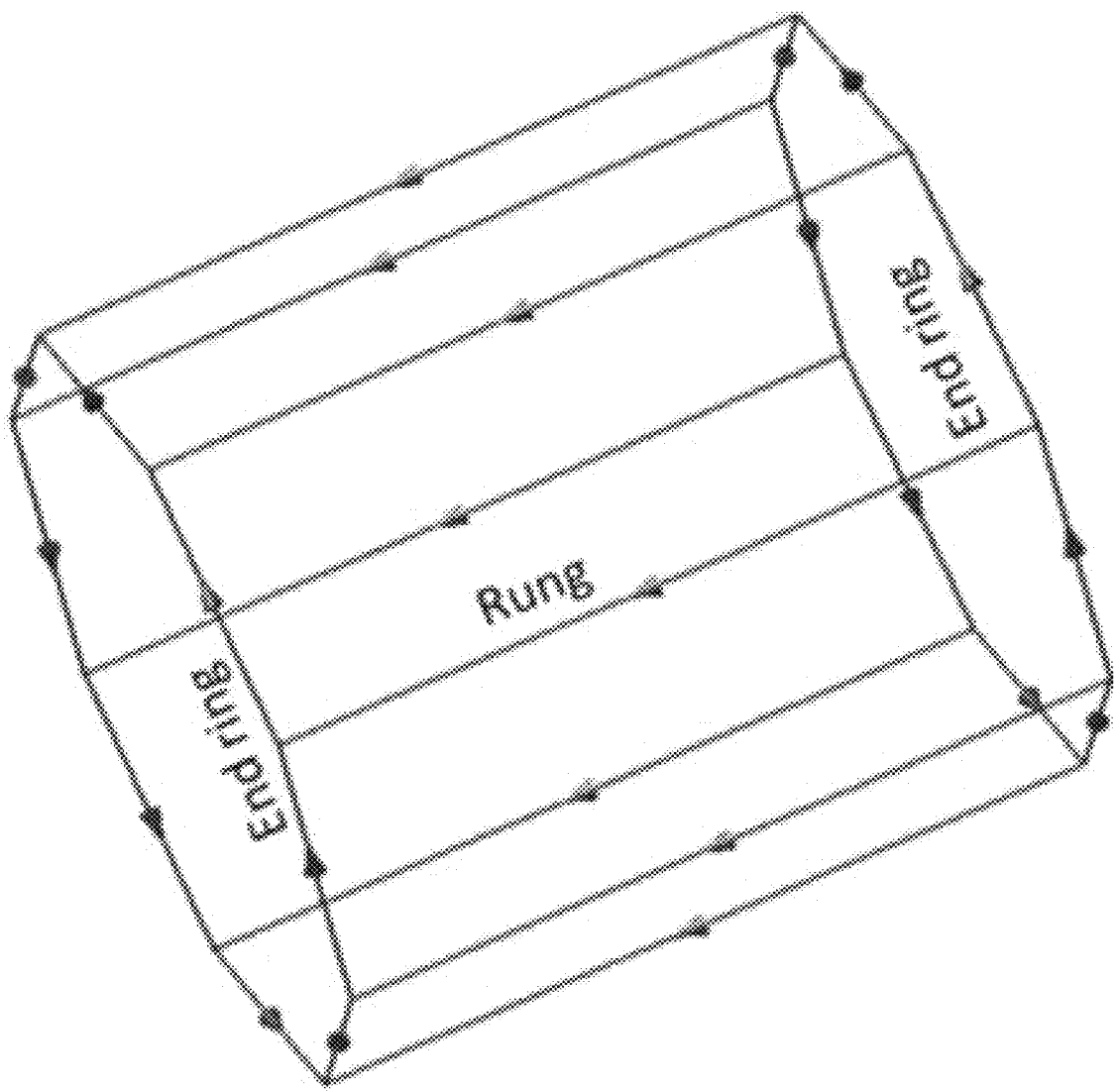
FIG. 4 demonstrates the structure of an MRI RF coil in simulation in accordance with an exemplary embodiment of the present invention.

A non-physical birdcage coil was designed to represent real MRI RF coil in simulation. FIG. 4 provides a perspective view of the structure of an MRI RF coil in simulation, which includes two end rings and eight rungs as labeled in the figure. In the example of the MI RF coil shown in FIG. 4, the diameter of the RF coil was 63 cm and the height of the RF coil was 65 cm. The eight parallel lines (rungs) were current sources. The end rings on the top and bottom of the RF coils were tuning capacitors. To generate a circular polarized electromagnetic field inside the coil, all current sources had a uniform magnitude. The phase difference between current sources on adjacent rungs was 2π/N, where N is the total number of rungs. All tuning capacitors had adjusted to 7.2 pF so that the coil was resonant at 64 MHz. Further details of the coil are provided in Lie et al., Electromagnetic Biology and Medicine, 2014, Vol. 33, No. 3, Pages 223-22.

SEMCAD X v14.8, commercial full-wave electromagnetic software based on Finite-Difference-Time-Domain (FDTD), was used in this simulation study. For post-processing, all field distributions were normalized to an input power so that the overall averaged SAR was 2 W/kg. The local SAR values were obtained at the maximum value inside the phantom.

D. Experimental Testing

Reduction of RF induced heating effect was also investigated experimentally. The temperature increase caused by the external fixation device, which was partly immersed into a standard ASTM phantom during MRI procedure, were measured to evaluate the effects of a newly introduced absorption material to reduce the RF induced heating. Polyacrylic acid (PAA) gelled saline was prepared as phantom material according to ASTM F2182-11a standard; the relative electric permittivity was about 80 and conductivity was measured to be 0.46 S/m.

A commercially available external fixation device, provided by Orthofix, Italy, was analyzed in this experiment. During the experimentation, the ASTM Phantom loaded with external fixation device was tested using a ZMT-Medical Implant Test System (MITS) MRI RF safety evaluation system. The ETS-Lindgren MRI shielding room was employed to prevent leakage of RF field. Up to 4 fiber-optical temperature probes were used to measure the heating. The temperature recording platform was embedded with the probe system so that there was no need for manual recording.

Figure 5A:
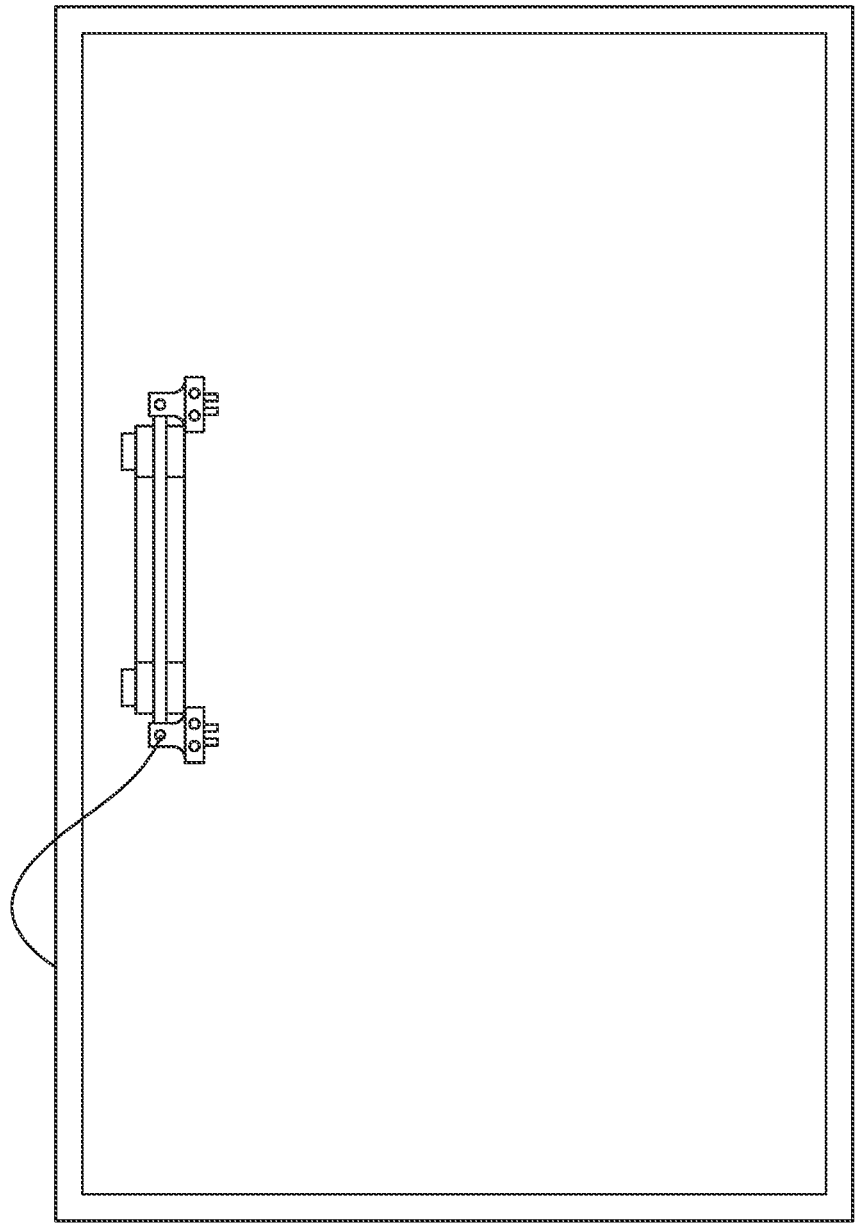
FIG. 5A shows the top view of an experimental setup for external fixation device and ASTM phantom in accordance with an exemplary embodiment of the present invention.
Figure 5B:
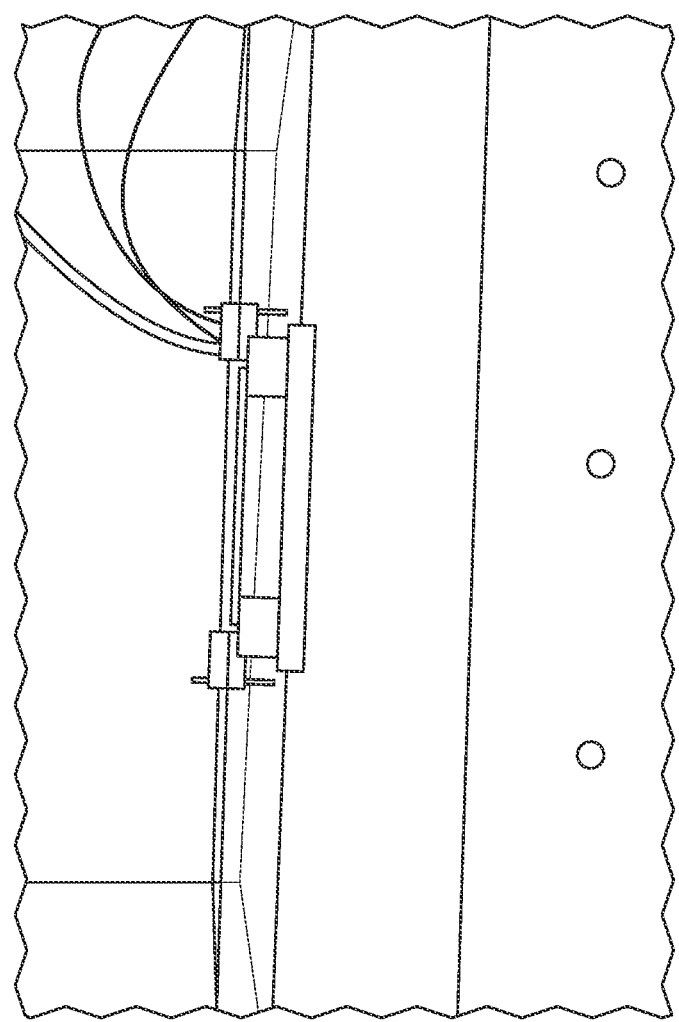
FIG. 5B shows the side view of an experimental setup for external fixation device and ASTM phantom in accordance with an exemplary embodiment of the present invention.
Figure 5C:
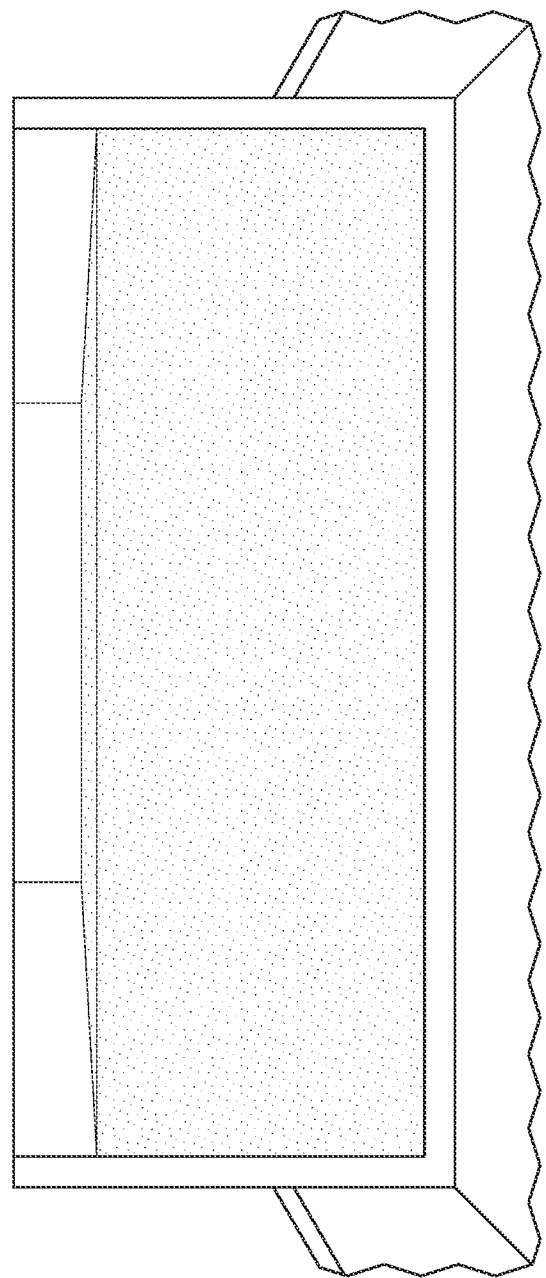
FIG. 5C shows the front view of an experimental setup for external fixation device and ASTM phantom in accordance with an exemplary embodiment of the present invention.
Figure 5D:
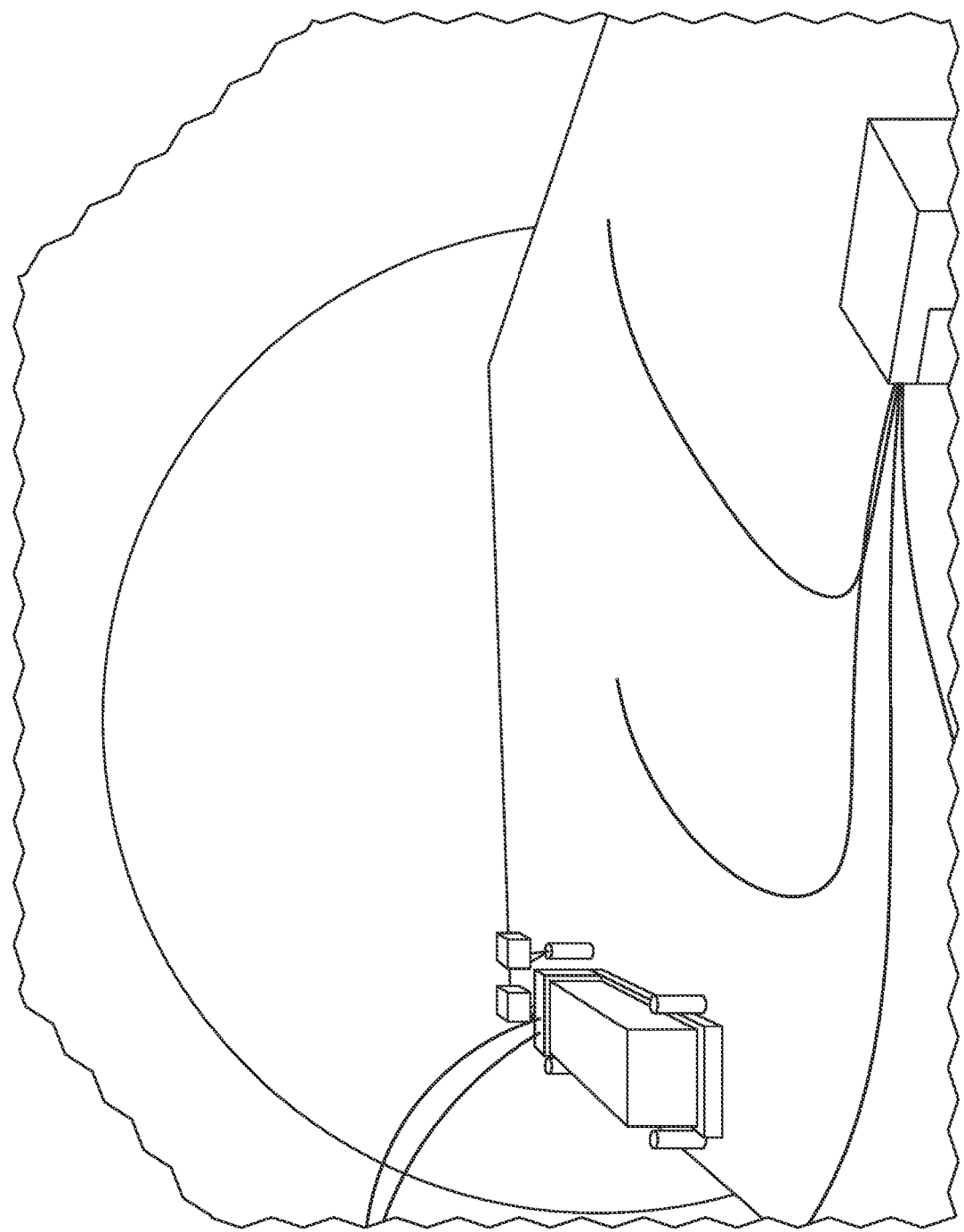
FIG. 5D shows an external fixation device placed into an ASTM phantom in accordance with an exemplary embodiment of the present invention.

According to standard ASTM F2182-11a, an external fixation device was put into phantom at about 2-3 cm from the side. FIGS. 5A-5D may provide different views of an experimental setup for external fixation device and ASTM phantom. FIG. 5A, FIG. 5B and FIG. 5C show the top view, the side view and the front view of the experimental setup for external fixation device and ASTM phantom. FIG. 5D shows the external fixation device being placed into the ASTM phantom. The phantom with the fixation device was exposed into MRI birdcage body coil for 15 minutes. The temperature was recorded 1 minute before the MRI coil was turned on and continuously recorded for 2 minutes after MRI system was turned off, for a total 18 minutes under MRI. The data were exported to computer for analysis.

There was a half-hour cooling procedure between two consecutive experiment measurements. The device was taken outside and cooled by water and the saline was stirred. With the help of this procedure, the initial conditions for each experiment were guaranteed to be consistent in each run.

E. Results from Simulations

For the simulation study, 5 categories of materials with different absorption characteristics were numerically examined. Each category had its individual dielectric constant εr=2, 3, 5, 7, 9, and the electrical conductivity varied from $10^{-4}$ to $10^3$ S/m. The electromagnetic properties of device bar, ASTM phantom gel, ASTM phantom shell are shown in Table 1. The other parts of the external fixation devices were modeled as perfect electric conductor (PEC). After the simulation, the 1 g spatial-averaged SAR along device pins were calculated for further analysis.

TABLE 1

Electrical Properties of Different Materials (at 64 MHz)

| | Relative Permittivity | Electrical Conductivity |
|---|---|---|
| ASTM Phantom Gel | 80.38 | 0.448 |
| ASTM Phantom Shell | 3.7 | 0 |
| Bar (Carbon fiber) | 10 | 5700000 |
| Device Clamp, Pin | PEC | PEC |

1) Typical Examples of Simulation

Figure 6:
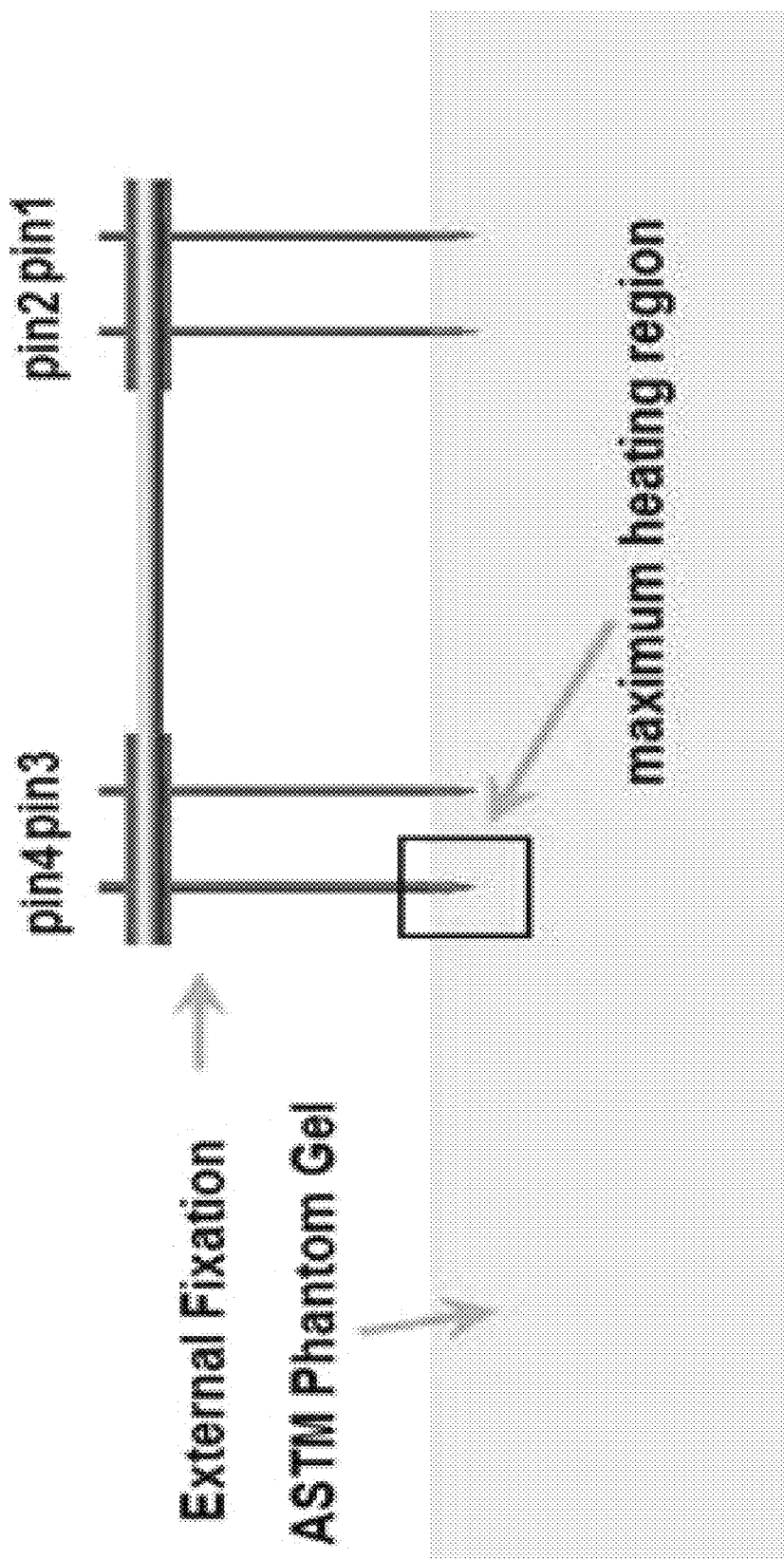
FIG. 6 shows a side view of external fixation device geometry in accordance with an exemplary embodiment of the present invention.
Figure 7A:
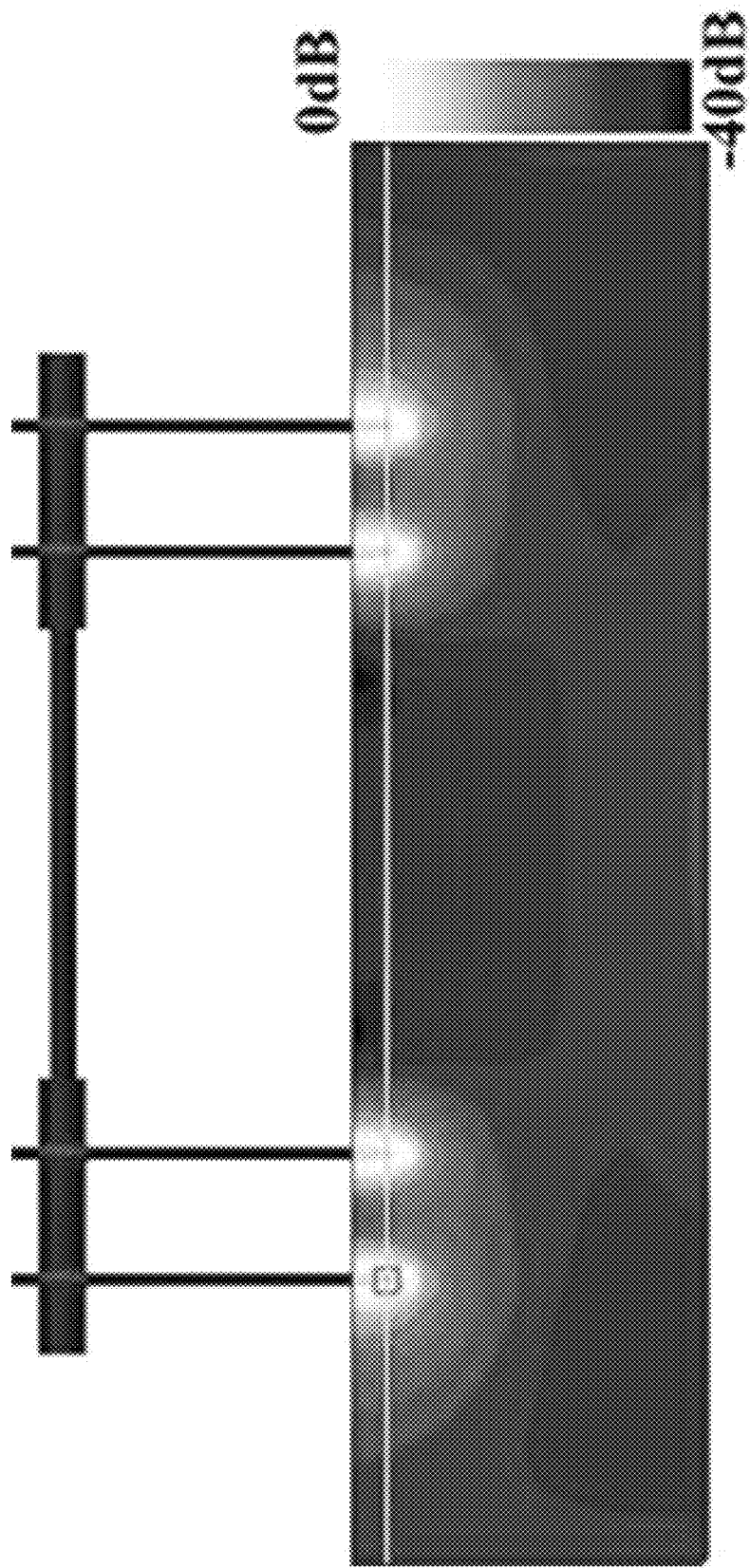
FIG. 7A shows 1 g average SAR distribution at a cross-section plane of pins using an absorption material with electrical conductivity of 0 S/m in accordance with an exemplary embodiment of the present invention.
Figure 7B:
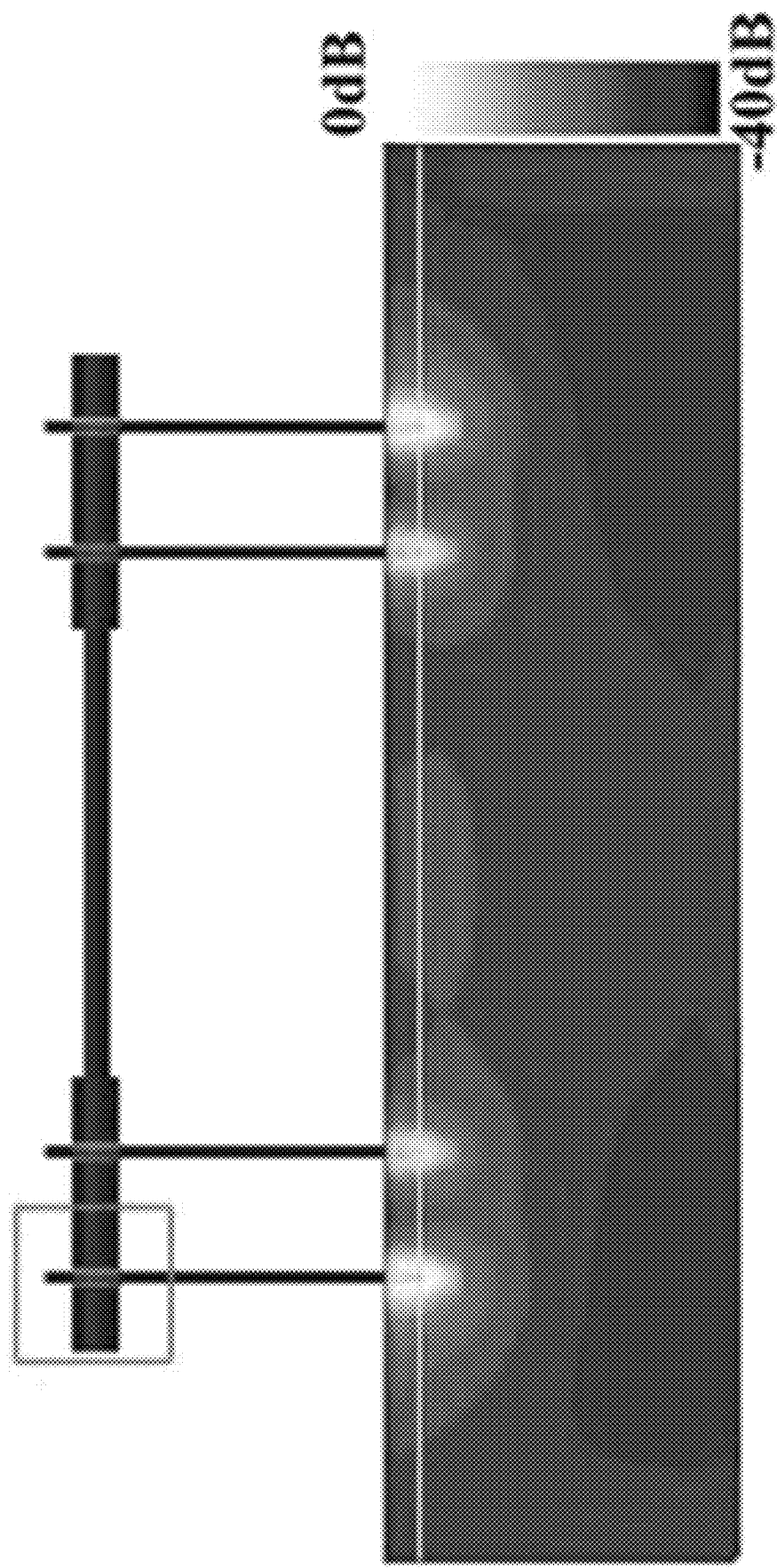
FIG. 7B shows 1 g average SAR distribution at a cross-section plane of pins using, an absorption material with electrical conductivity of 0.1 S/m in accordance with an exemplary embodiment of the present invention.
Figure 8:
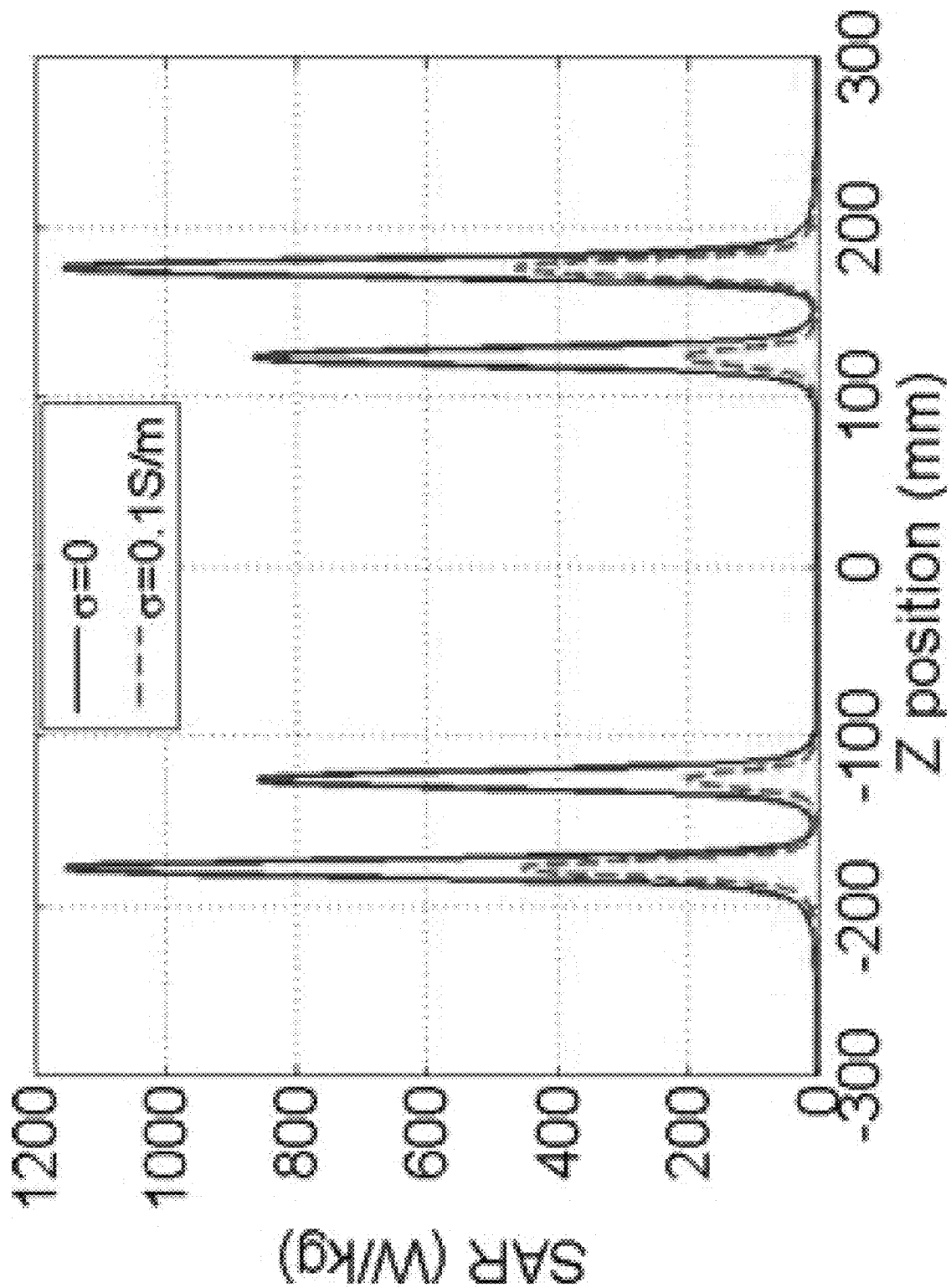
FIG. 8 shows SAR along the line that across the tips of pins in accordance with an exemplary embodiment of the present invention.

Shown in FIG. 6 is a side view of an exemplary external fixation device that includes four pins. For simplicity, the four pins are named pin 1, pin 2, pin 3, and pin 4 from right to left. Two examples were chosen to illustrate typical SAR patterns. The first example is shown in FIG. 7A. The absorption material had a dielectric constant $\varepsilon r$ of 9 and an electrical conductivity $\sigma$ of 0 S/m. The maximum heating regions occurred at the tip of the pins. The square at a pin tip in this figure denotes the maximum local SAR. To have a better view, the SAR along a horizontal line across the pin tips (the green line in FIG. 7A connecting all pin tips) is shown in FIG. 8. It is observed that the points near the outer pins (pin 1 and pin 4) have larger SAR value than that at the inner pins (pin 2 and pin 3). The highest SAR could be as high as 1160 W/kg, which was located at the tip of pin 4. In the second example, the absorption material had a dielectric constant $\varepsilon r$ of 9 and an electrical conductivity $\sigma$ of 0.1 S/m. The SAR pattern is shown in FIG. 7B. The SAR pattern inside the phantom gel was similar as before, but the peak SAR near the tips were significantly different and the maximum local SAR occurred at the layer of absorption materials between clamp and pin (and not at the pin tip), as denoted by a square in FIG. 7B. The SAR value along the same green line connecting all pin tips is plotted in FIG. 8. While the maximum local SAR was 905 mW/g, the maximum local SAR inside the phantom was about 470 mW/g. Since only inside the phantom was the region of interest, the max SAR was reduced by nearly 59.5% as compared to pure insulating material. This significant heat reduction signals a major breakthrough for clinical applications.

Those field distributions in FIG. 7 were normalized to 1160 W/kg. No matter what the absorption material was, the energy dissipation was found to be concentrated and decayed rapidly around the tip of the pin. When $\varepsilon r=9$ and $\sigma=0.1$ S/m, the maximum SAR at the tip of the pin was smaller than that when $\varepsilon r=9$ and $\sigma=0$ S/m. This implies absorption materials with optimized dielectric properties can significantly reduce, if not entirely eliminate, RF induced heating in external fixation devices.

2) Max SAR-Conductivity Carves Vs. Permittivity

Figure 9:
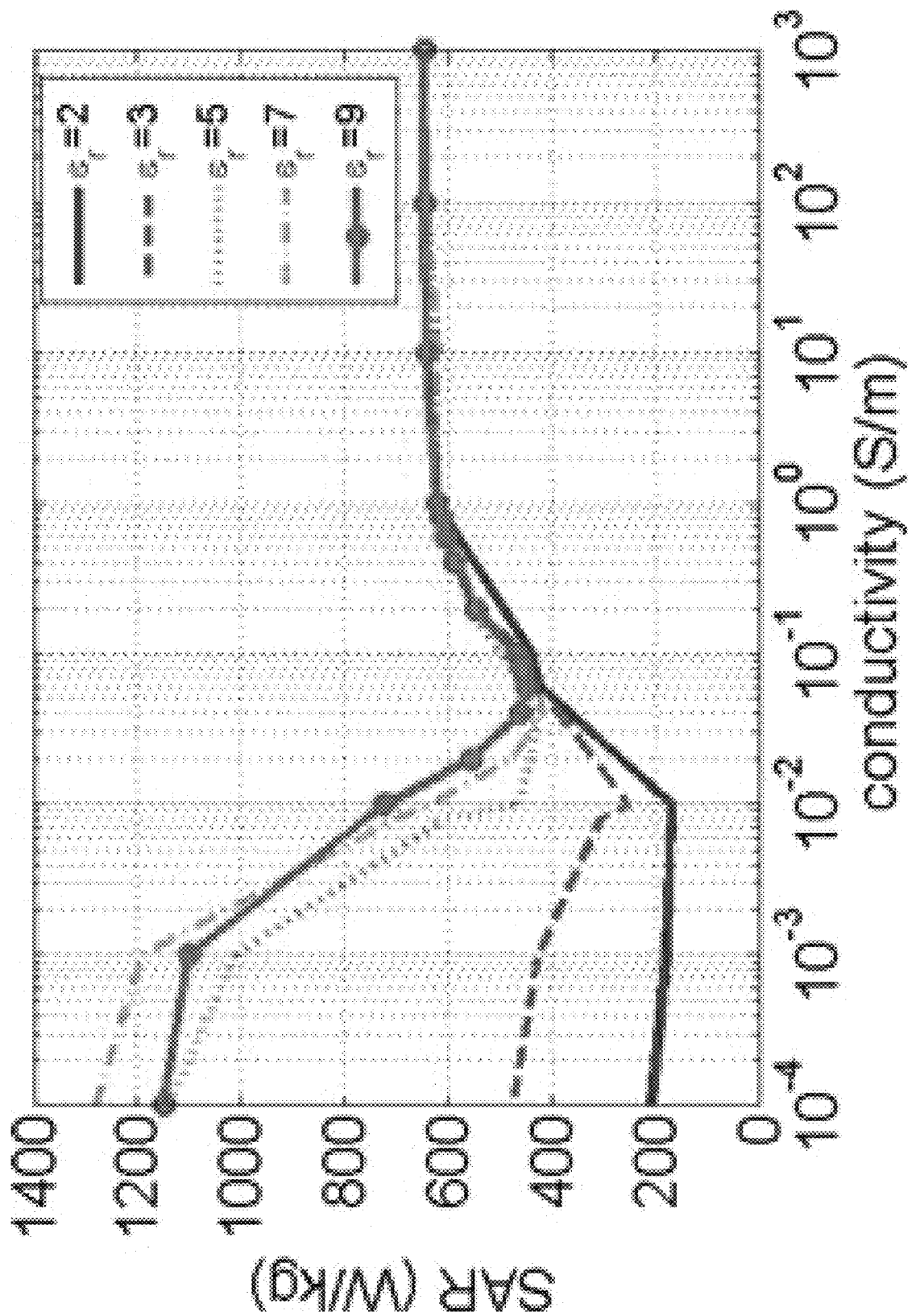
FIG. 9 shows the maximum local SAR near pin tip vs. conductivity for different dielectric constant in accordance with an exemplary embodiment of the present invention.

For this specific geometry change of the conductivity and permittivity of the absorption material brought different thermal behaviors to the external fixation device. As shown in FIG. 9, a significant reduction in RF induced heating was found in the general range of greater than $10^{-4}$ S/m, particularly from $10^{-4}$ to 1000 S/m, more particularly from $10^{-3}$ to 1 S/m, and even more particularly from $10^{-2}$ to 1 S/m. Outside these ranges the maximum local SAR increased for all investigated permittivity values: $\varepsilon r=2, 3, 5, 7,$ and 9. It should be pointed out that the current optimal conductivity for a 64 MHz application was achieved for an absorption material thickness of 1 mm. This optimal conductivity could change with the absorption material thickness.

Various dielectric constants were tried to test the idea of using different absorption materials. It can be seen from FIG. 9 that utilization of an absorption material could effectively reduce RF heating in an external fixation device for a large permittivity range (from 2 to 9). For a smaller permittivity, the conductivity needed to reach the minimum SAR was smaller. For this example an optimum absorption material, i.e., minimum heating, had the following, dielectric properties: $\varepsilon r=2$ and $\sigma=10^{-2}$ S/m.

Referring back to FIG. 1, a RF heating during MRI scanning at the insert, particularly at the portion of the insert that is within the patient's tissue/bone, such as a tip of an insert pin, is significantly reduced as compared to the RF heating in the absence of the absorption material 14. By "significantly reduced", it is intended to mean that the SAR with the absorption material 14 is less than 90% of the corresponding SAR without the absorption material 14, for example, less than 85%, or less than 80%, less than 75%, less than 70%, less than 65%, less than 55%, less than 45%, less than 35%, less than 25%, or less than 15%.

F. Experimental Results in RF Heating Reduction

Figure 10A:
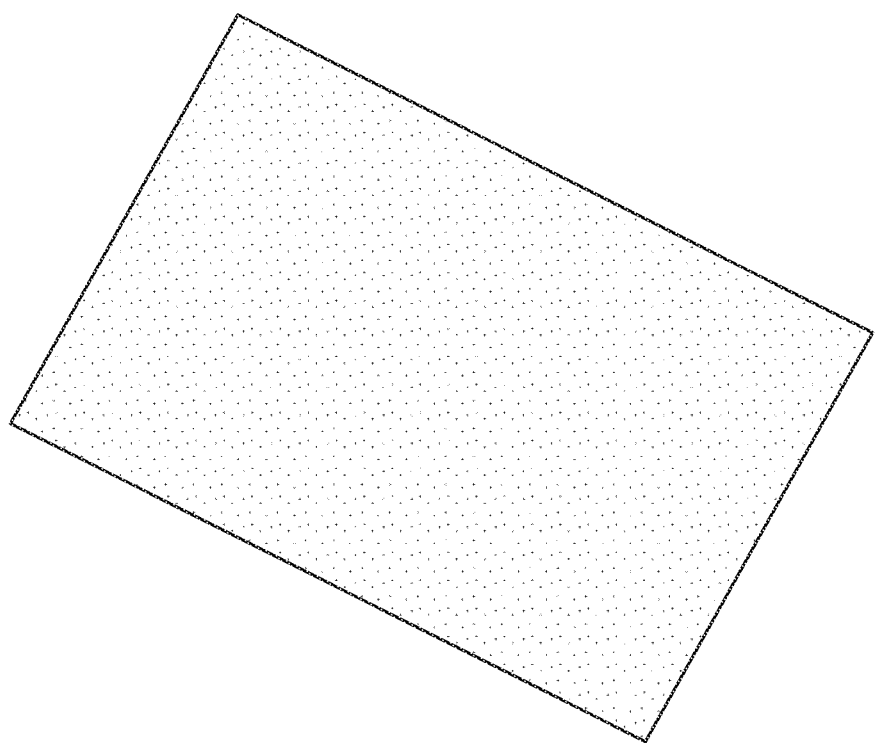
FIG. 10A shows the front side of an absorption material in the form of a film in accordance with an exemplary embodiment of the present invention.
Figure 10B:
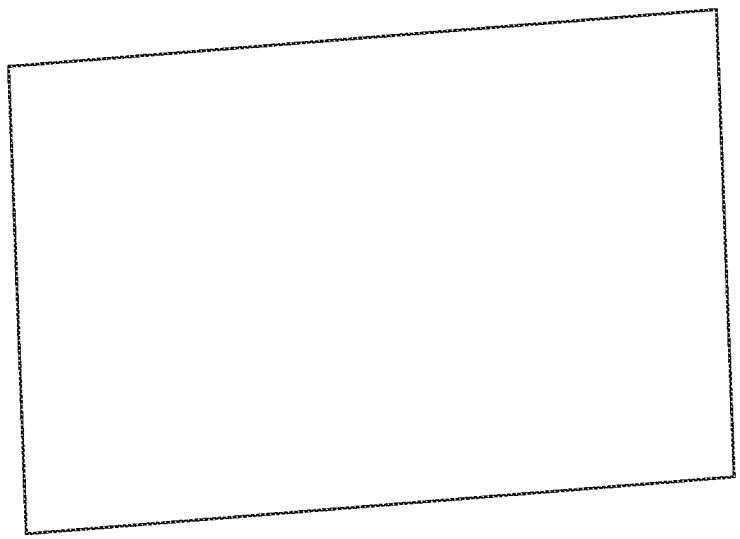
FIG. 10B shows the back side of an absorption material in the form of a film in accordance with an exemplary embodiment of the present invention.
Figure 10C:
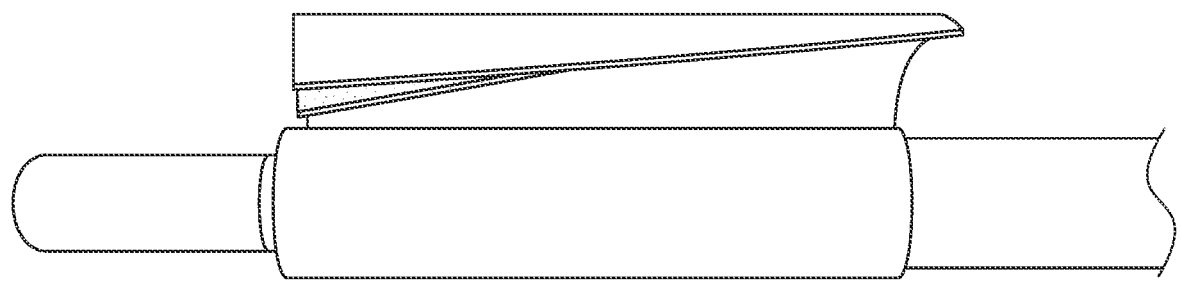
FIG. 10C shows an absorption material film is wrapped around a pin in accordance with an exemplary embodiment of the present invention.
Figure 10D:
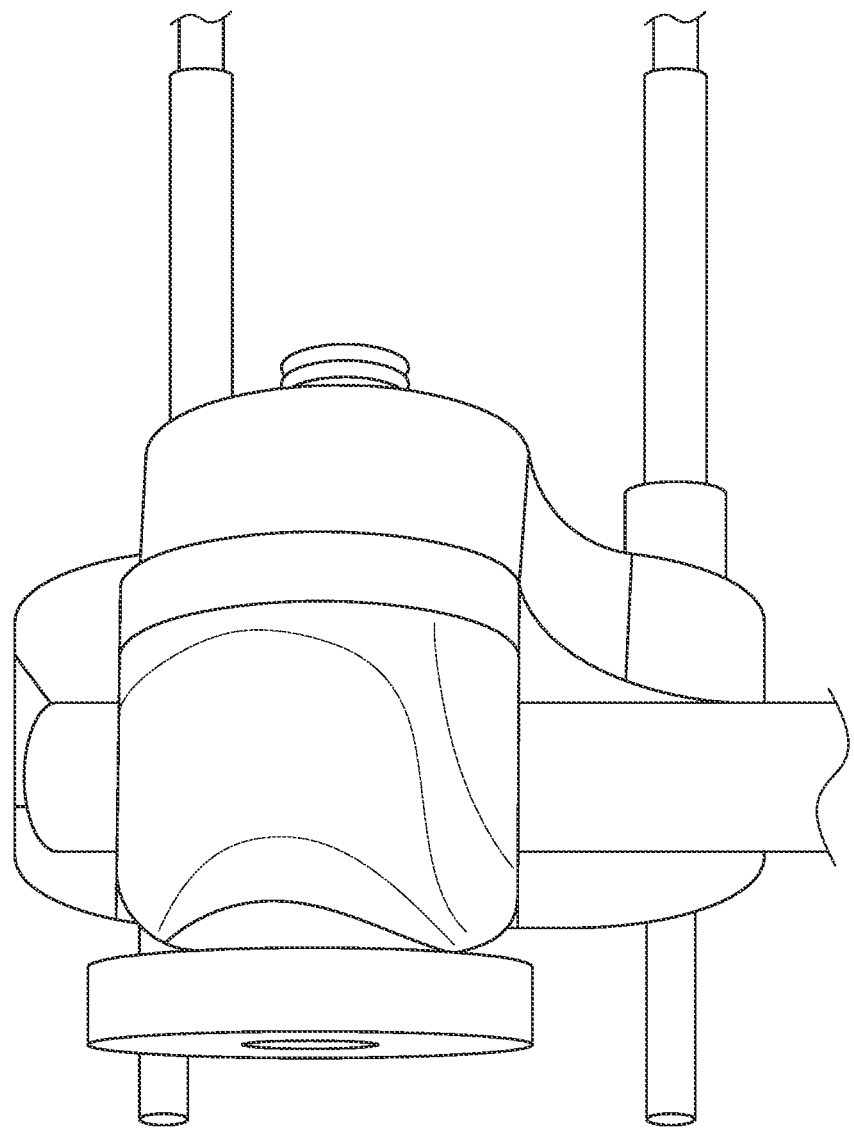
FIG. 10D shows a pin wrapped with an absorption material film is fastened to a clamp in accordance with an exemplary embodiment of the present invention.

For testing, an absorption material provided by Molex Incorporated (Lisle, Ill.) was wrapped at connecting part between device components with 1 mm thickness, as shown in FIGS. 10A-10D. FIGS. 10A-10C provide top views of different parts of a setup, and FIG. 10D provides the setup itself for absorption in an external fixation device. Specifically, FIG. 10A shows the front side of the absorption material in the form of a film, while FIG. 10B shows its back side. In FIG. 10C, the absorption material film is wrapped around a pin. Then, the pin wrapped with the absorption material film is fastened to a clamp, as shown in FIG. 10D.

There were two kinds of connecting parts. One was covered between the clamps and the pins, and the other one was covered between the clamps and the bars. For convenience, these two configurations are named (and so labelled in FIG. 11) as "pin cover" and "bar cover", respectively.

The following four different covering examples were measured in the experimental study: (1) No cover for device (no cover); (2) Cover between pin and clamp (pin cover); (3) Cover between clamp and bar (bar cover); and (4) Covers on both sides (both cover).

Figure 11:
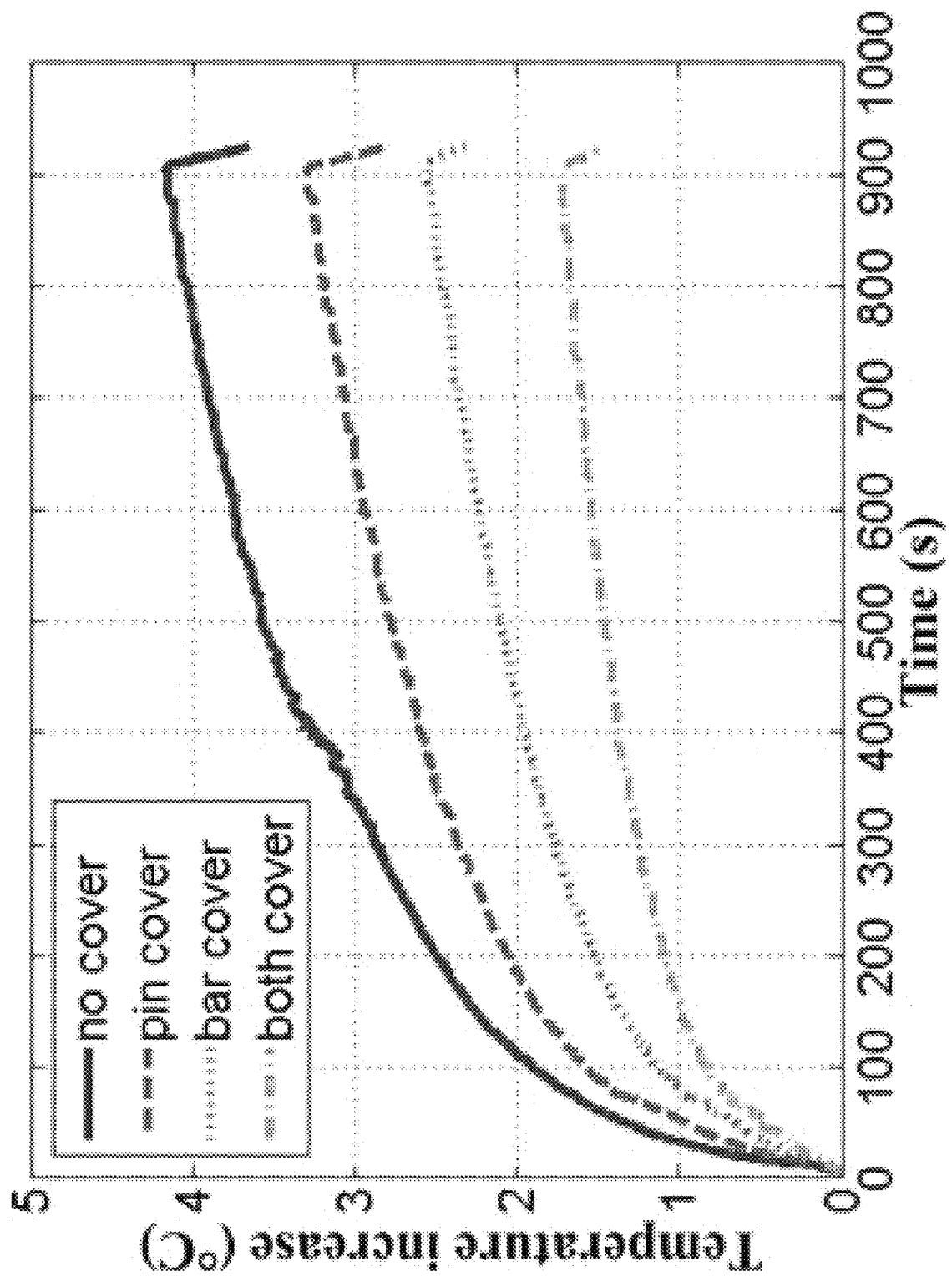
FIG. 11 shows measurement results of temperature increase over time for 4 tested cases in accordance with an exemplary embodiment of the present invention.

The temperature increases detected for all 4 covering examples are plotted in FIG. 11. The device with no cover (dark blue continuous line) was observed to have the greatest temperature increase, about 4.2° C. As the pin cover (green dashed line) or bar cover (red dotted line) applied to the external fixation device, the heating effect became less significant (3.3 and 2.6° C., respectively). The device with covers on both sides (light blue dashed-dotted line) had the lowest temperature increase (as low as 1.7° C.).

The present invention further provides a method for reducing RF-induced heating in an external fixation device comprising:

(1) providing an external fixation device comprising at least an insert for inserting into a tissue such as a bone and a fastening assembly, wherein the fastening assembly comprises at least a RF heat source member;

(2) covering at least a part of the member's surface with an absorption material to reduce the transfer of RF induced heat from the member to the pin directly or indirectly, wherein the absorption material has an electric conductivity greater than $10^{-4}$ S/m; and (3) fastening the insert to the fastening assembly.

The method may further include a step of MRI scanning a patient with the external fixation device.

In the foregoing specification, embodiments of the present invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicant to be the scope of the invention, is the literal and equivalent scope of the set of claims that issue from this application, in the specific form in which such claims issue, including any subsequent correction.

The invention claimed is:

1. An external fixation device comprising:
at least one insert for inserting into a tissue; and
a fastening assembly for securing the at least one insert in a desired position for the external fixation device, wherein the insert is fastened to the fastening assembly;
wherein further the fastening assembly comprises at least one RF heat source member external to the tissue that allows RF induced heating when subjected to RF signals,
other components of the fastening assembly that assemble together with the RF heat source member, and
an RF heating absorption material covering any interfaces between the RF heat source member and the other components of the fastening assembly, wherein the RF heating absorption material reduces transfer or dissipation of the RF induced heating from the RF heat source member to the insert directly or indirectly, and wherein the RF heating absorption material has an electric conductivity greater than $10^{-4}$ S/m and lower than $10^3$ S/m.

2. The external fixation device according to claim 1, wherein the insert is a pin, a through wire, a screw, or any combination thereof.

3. The external fixation device according to claim 1, wherein the RF heat source member in the fastening assembly is selected from rods, bars, rings, clamps, threaded rods and nuts, wire bolts, connection bolts/joints, external fixation pins, standoffs, locking hinges, angular distractors, linear distractors, connecting plates, speed nuts, supports, washers, and any combination thereof.

4. The external fixation device according to claim 1, wherein the RF heating absorption material is in the form of a film, a layer, a cushion, a coating, and a seal tape.

5. The external fixation device according to claim 1, wherein the RF heating absorption material is an intermediate layer or an interfacial film between the RF heat source member and the other components of the fastening assembly that would directly contact the RF heat source member in the absence of the layer or film.

6. The external fixation device according to claim 1, wherein the RF heating absorption material is an intermediate layer or an interfacial film between the insert and the RF heat source member that would directly contact the insert in the absence of the layer or film.

7. The external fixation device according to claim 1, wherein the RF heating absorption material is an intermediate layer or an interfacial film between the insert and a component other than the RF heat source member in the fastening assembly that would directly contact the insert in the absence of the layer or film.

8. The external fixation device according to claim 1, wherein the RF heating absorption material has a dielectric constant εr in the range of about 4-9.

9. The external fixation device according to claim 1, wherein the RF heating absorption material has a dielectric constant εr in the range of about 1-4.

10. The external fixation device according to claim 1, wherein the RF heating absorption material has a thickness of not greater than 10 mm.

11. A method for reducing RF-induced heating in an external fixation device comprising:
(1) providing an external fixation device comprising
at least an insert for inserting into a tissue,
a fastening assembly for securing the at least one insert in a desired position for the external fixation device, wherein the fastening assembly comprises at least a RF heat source member that reduces transfer or dissipation of the RF-induced heating from the RF heat source member to the insert directly or indirectly, and other components of the fastening assembly that assemble together with the RF heat source member;
(2) covering any interfaces between the RF heat source member and the other components of the fastening assembly with an RF heating absorption material, wherein the absorption material has an electric conductivity greater than $10^{-4}$ S/m and lower than $10^3$ S/m; and
(3) fastening the insert to the fastening assembly.

12. The method according to claim 11, further comprising a step of MRI scanning a patient with the external fixation device.

13. The method according to claim 11, wherein the insert is a pin, a through wire, or a screw; and wherein the RF heat source member in the fastening assembly is selected from rods, bars, rings, clamps, threaded rods and nuts, wire bolts, connection bolts/joints, external fixation pins, standoffs, locking hinges, angular distractors, linear distractors, connecting plates, speed nuts, supports, and washers.

14. The method according to claim 11, wherein the RF heating absorption material is in the form of a film, a layer, a cushion, a coating, a seal tape, or any combination thereof; and is placed between the RF heat source member and the other components of the fastening assembly that would directly contact the RF heat source member in the absence of the absorption material.

15. The method according to claim 11, wherein the RF heating absorption material is in the form of a film, a layer, a cushion, a coating, a seal tape, or any combination thereof; and is placed between the insert and the RF heat source member that would directly contact the insert in the absence of the absorption material.

16. The method according to claim 11, wherein the RF heating absorption material is in the form of a film, a layer, a cushion, a coating, a seal tape, or any combination thereof; and is placed between the insert and a component other than the RF heat source member in the fastening assembly that would directly contact the insert in the absence of the absorption material.

* * * * *